United States Patent

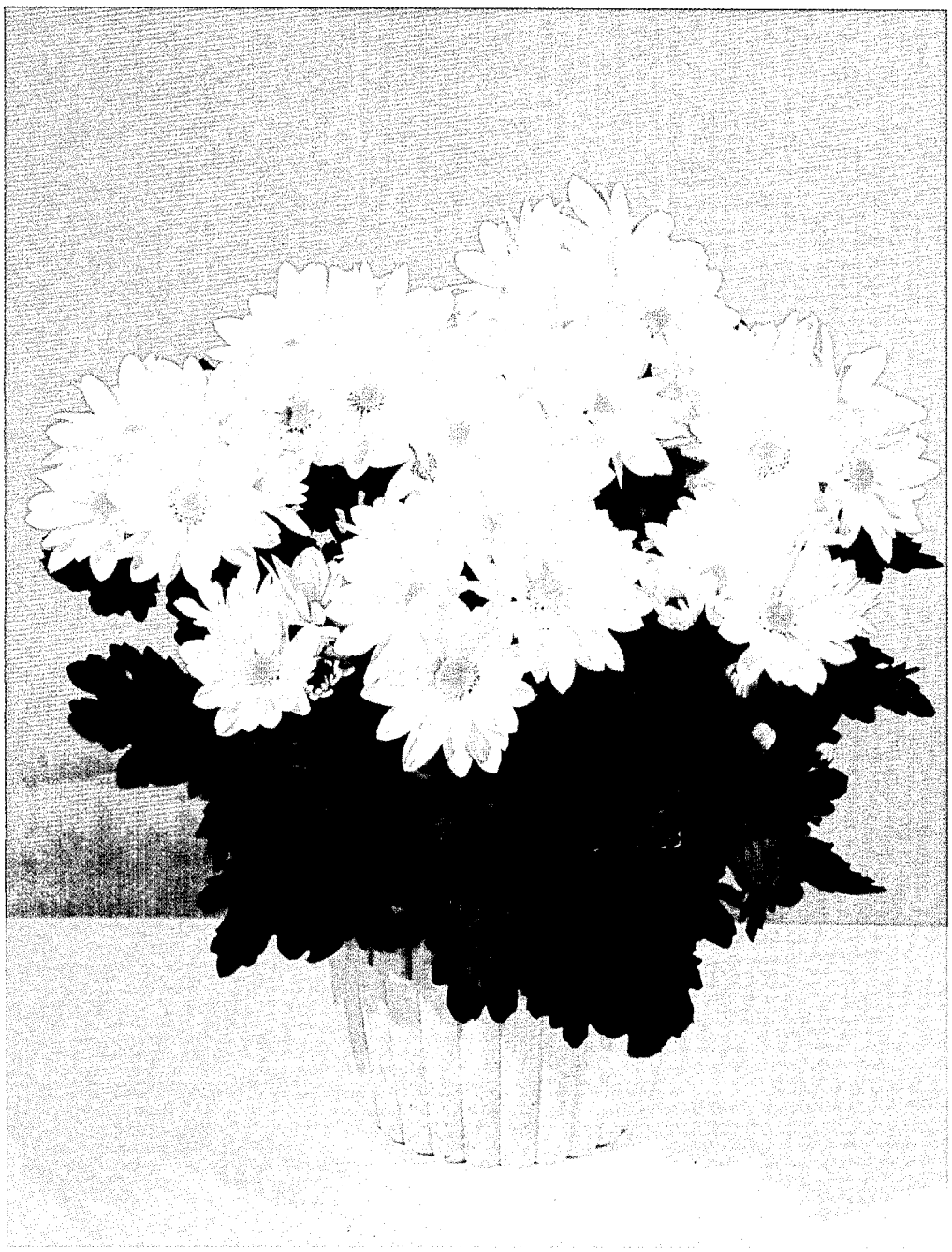

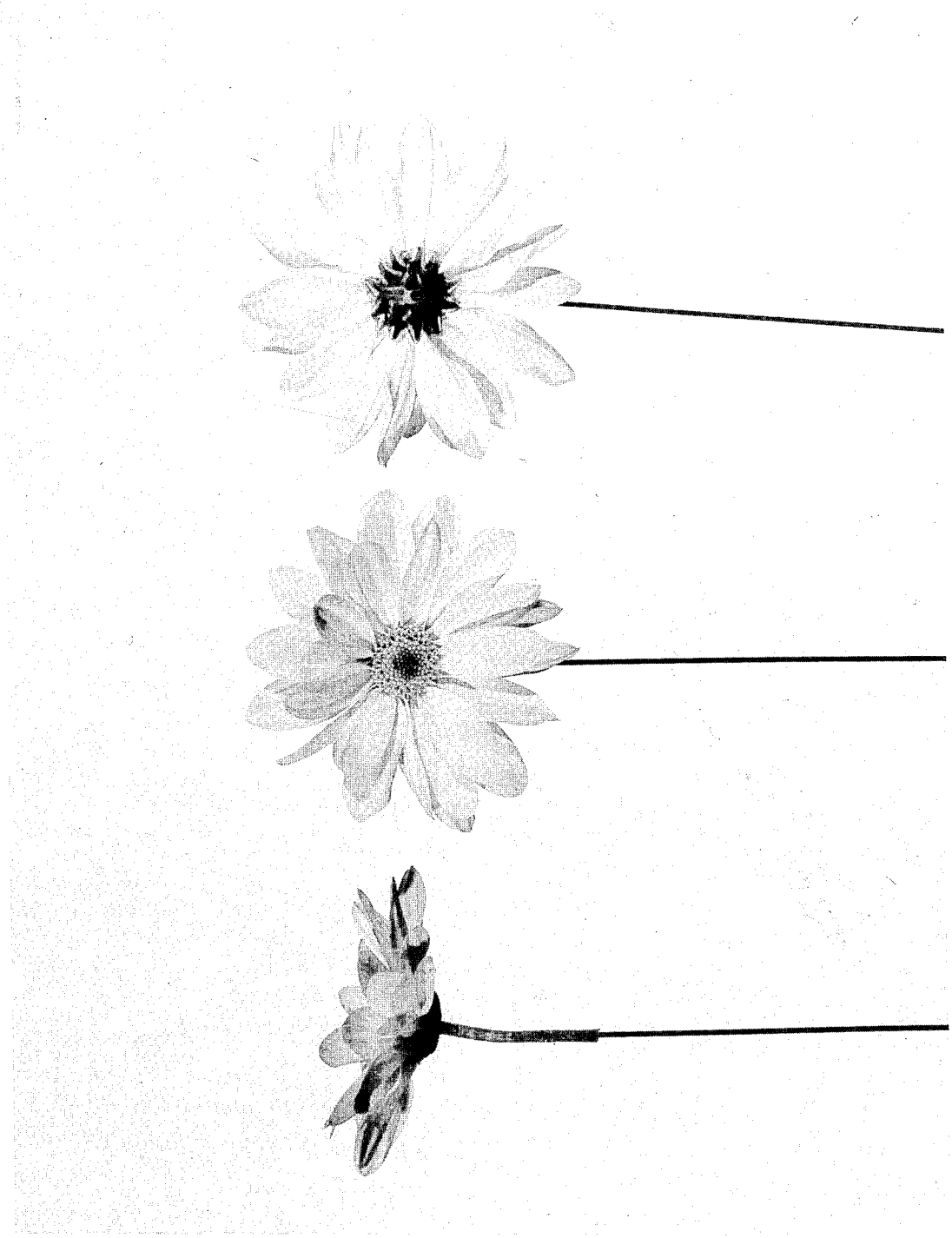

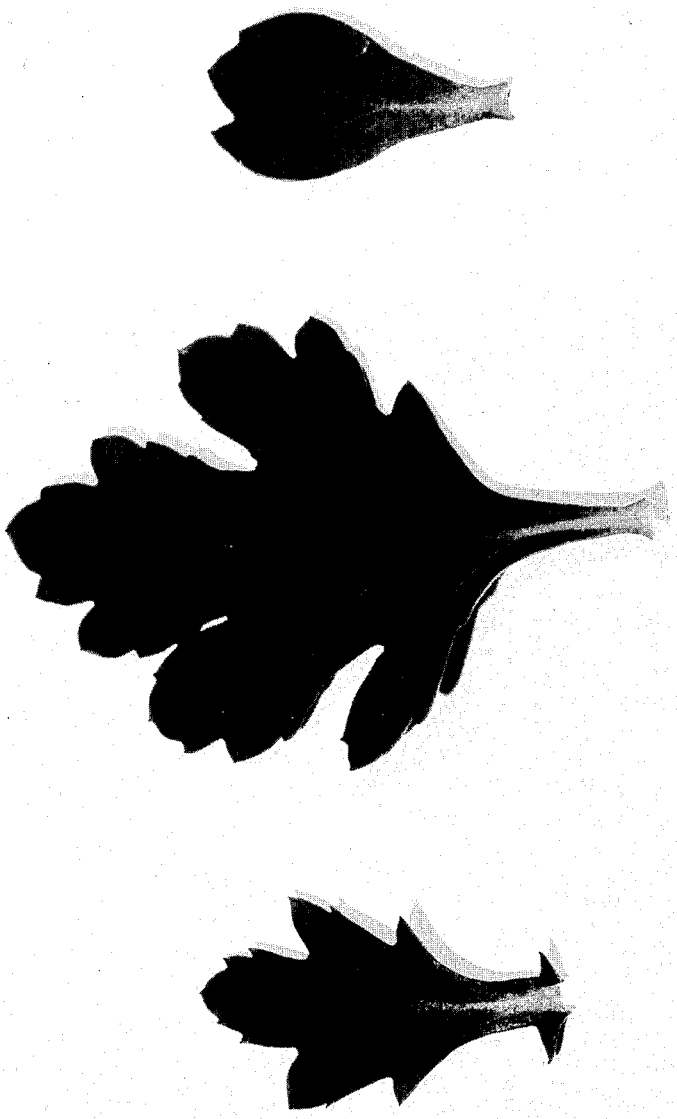

Plant Pat. 3,863
Patented Apr. 13, 1976

3,863

CHRYSANTHEMUM PLANT

Walter H. Jessel, Jr., Doylestown, and William E. Duffett, Akron, Ohio, assignors to Yoder Brothers, Inc., Barberton, Ohio

Filed Feb. 21, 1975, Ser. No. 551,838
Int. Cl. A01h *5/00*
U.S. Cl. Plt.—74 1 Claim

The present invention comprises a new and distinct cultivar of *Chrysanthemum morifolium,* Ramat., hereinafter referred to by the cultivar name Ritz (#70123013).

Ritz was originated from a cross made in a controlled breeding program in Barberton, Ohio in the year 1969. The female, or seed parent, was #67100005 (unnamed seedling), a daisy of yellow color originated by the present inventors from a cross between Tuneful (#54285007; unpatented; commercially available) and #65741001 (unnamed seedling). Both parents were products of the breeding program of the present inventors.

The male, or pollen parent, was Dramatic (#67079001; U.S. Plant Pat. #3,189), a daisy of bronze color originated by the present inventors from a cross between Dazzler (#65093001; unpatented; commercially available) and #65013002 (unnamed seedling). Both parents were products of the breeding program of the present inventors.

Ritz was discovered and selected as a flowering seedling within the progeny of the stated cross by William E. Duffett and Walter H. Jessel, Jr. on July 9, 1970 in a controlled environment in Barberton, Ohio.

Ritz is a product of a planned breeding program which had the objective of creating a durable yellow daisy adaptable to pot chrysanthemum culture that would fulfill in part or in whole the need for a yellow daisy companion to the variety Dramatic with uniform eight to nine week response and the ability to produce commercial quality in year round flowering programs when grown as a pinched spray pot plant.

The first act of asexual reproduction of Ritz was accomplished when vegetative cuttings were taken from the initial seedling in September 1970 in a controlled environment in Barberton, Ohio by a technician under formulations established and supervised by William E. Duffett and Walter H. Jessel, Jr.

Continued asexual reproduction by vegetative cuttings for evaluative tests in flowering and stock programs in conjunction with horticultural certification initiated Apr. 16, 1971 at Barberton, Ohio have demonstrated that the combination of characteristics as herein disclosed for Ritz are firmly fixed and are retained through successive generations of asexual reproduction.

The following descriptive observations, measurements, and comparisons were derived from plants grown as pinched spray pots in a greenhouse in Barberton, Ohio under conditions which closely approximate those generally used in commercial practice (as defined in Chart A and Chart B which appear at the end of the present specification).

The following traits have been repeatedly observed and are determined to be basic characteristics of Ritz which in combination distinguish this chrysanthemum as a new and distinct cultivar:

1. Daisy inflorescence type.
2. Flat inflorescence form not known to reflex.
3. Diameter of face of inflorescence up to three inches at maturity.
4. Medium yellow ray floret color devoid of bronze tinging with minimal color oxidation.
5. Medium green disc floret color at immature, unopened stage.
6. Minimal pollen development.
7. Uniform nine week response period.
8. Durable flowers and foliage lasting up to 28 days under average home temperatures of 68° to 75° F.
9. Adaptability to a wide range of pot sizes due to responsiveness of height to day length and B–9.

The accompanying photographic drawings show typical inflorescence and foliage characteristics of Ritz, with colors being as nearly true as possible with color illustrations of this type. Sheet 1 is a color photograph of Ritz as a specimen pot. Sheet 2 is a black and white photograph showing three different views of the inflorescence of Ritz. Sheet 3 is a black and white photograph showing the foliage of Ritz at various stages of growth.

The phenotype of Ritz may vary significantly with variations in environment such as temperature, light intensity, and daylength outside the ranges defined in Chart A and Chart B. The genotype of Ritz was not observed under all possible environments.

Known commercially available cultivars with which Ritz may appropriately be compared are Pride (U.S. Plant Pat. #3,597), Improved Yellow Bonnie Jean (U.S. Plant Pat. #3,404), and Bright Yellow Tuneful (unpatented). Reference is made to attached Chart C which compares certain characteristics of the above mentioned cultivars with the same characteristics of Ritz. Further comparisons are as follows:

1. In comparison to Pride, Ritz has a lighter yellow ray floret color, a larger diameter across the face of the inflorescence, and a more spreading branching habit. The height, the response period, and the inflorescence form and type of Ritz are the same as those of Pride.

2. In comparison to Improved Yellow Bonnie Jean, Ritz has a darker yellow ray floret color, a shorter height, and a shorter response period. The diameter across the face of the inflorescence, the spread of the branching habit, and the inflorescence form and type of Ritz are the same as those of Improved Yellow Bonnie Jean.

3. In comparison to Bright Yellow Tuneful, Ritz has a lighter yellow ray floret color, a shorter height, a more spreading branching habit, and a shorter response period. The diameter across the face of the inflorescence and the inflorescence form and type of Ritz are the same as those of Bright Yellow Tuneful.

In the following description, color references are made to The Munsel Limit Color Cascade, 1972 edition. The color values were determined between 3:00 p.m. and 3:30 p.m. on Aug. 14, 1974 under 200 foot candle light intensity at Barberton, Ohio.

Botanical classification: *Chrysanthemum morifolium*, Ramat., cv Ritz.

I. INFLORESCENCE

A. Capitulum:
- *Form.*—Flat.
- *Type.*—Daisy.
- *Permanence.*—21–28 days.
- *Diameter across face.*—2¾–3 inches.

B. Corolla of ray florets:
- *Texture (adaxial).*—Glabrous.
- *Appearance and form.*—Ligulate.
- *Arrangement.*—Whorled on receptacle.
- *Persistence.*—Resists shatter.
- *Color.*—Base: 23–9. Abaxial: 26–6 to 26–5. Adaxial: between 26–4 and 26–5.

C. Corolla of disc florets: Gamopetalous; tubular; 5-lobed.
- *Color.*—23–9 to 26–8.

D. Reproductive organs:
- *Androecium.*—Present both ray and disc florets.
- *Stamen.*—Syngenesious; 5 in number.
- *Pollen.*—Scant.
- *Gynoecium.*—Present both ray and disc florets.
- *Ovary.*—Inferior; bicarpellate.
- *Style.*—Single.
- *Stigma.*—2 lobed.

II. PLANT

A. General appearance: Semi-spreading; short.

B. Duration and Texture: Perennial; herbaceous.

C. Foliage:
- *Color.*—Abaxial: between 20–14 and 20–15. Adaxial: 21–11, but more greyed.
- *Shape.*—Spatulate: slightly lobed.
- *Texture.*—Glabrous.
- *Arrangement.*—Alternate.
- *Veination.*—Prominent.
- *Margin.*—Slightly serrated.

CHART A.—AVERAGE GREENHOUSE CHRYSANTHEMUM ENVIRONMENTS USED FOR BARBERTON, OHIO

| Season | Temperatures used, °F. Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: On, 5:30 p.m.—Off, 7:30 a.m. | From Oct. 15, 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: On, 5:30 p.m.—Off, 7:30 a.m. | To Apr. 15, 300 p.p.m. |
| Summer | 62 to 68 | 70 to 90 | 65 to 75 | 1 to 2 weeks at 3 hours per night of 7–10 f.c. | On, 6:00 p.m.—Off, 8:00 a.m. | None. |

NOTE.—For intensity of direct solar radiation, refer to Chart B.

CHART B

INTENSITY OF DIRECT SOLAR RADIATION

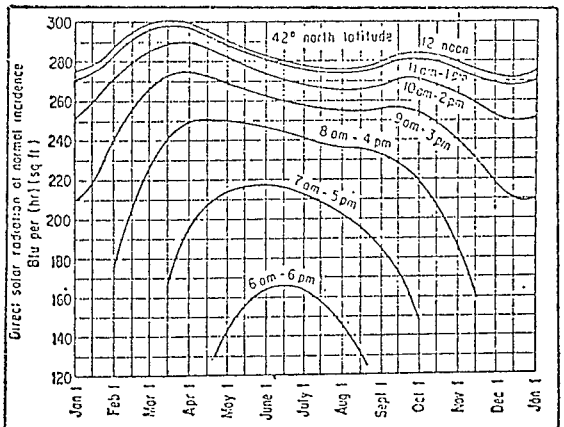

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C.—COMPARISON OF RITZ WITH PRIDE, IMPROVED YELLOW BONNIE JEAN AND BRIGHT YELLOW TUNEFUL

| Cultivar | Ray floret color | Diameter across face of inflorescence, inches | Height | Branching habit | Response period | Inflorescence form and type |
|---|---|---|---|---|---|---|
| Ritz | Medium yellow | 2¾–3 | Short | Semi-spreading | 9 weeks | Flat daisy. |
| Pride | Dark yellow | 2¼–2¾ | do | Semi-upright | do | Do. |
| Improved Yellow Bonnie Jean | Light yellow | 2¾–3 | Tall | Semi-spreading | 10 weeks | Do. |
| Bright Yellow Tuneful | Dark yellow | 2¾–3 | do | Semi-upright | do | Do. |

NOTE.—Comparisons made of plants grown in a greenhouse in Barberton, Ohio under conditions as defined in Chart A and Chart B.

We claim:

1. A new and distinct cultivar of chrysanthemum plant particularly characterized as to uniqueness by the combined features of daisy inflorescence type and flat inflorescence form which does not reflex; inflorescence diameter up to three inches at maturity; medium yellow ray floret color devoid of bronze tinging with minimal color oxidation; medium green disc floret color at immature, unopened stage; minimal pollen development; uniform nine week response period; durable flowers and foliage; and adaptability to a wide range of pot sizes under a controlled environment.

No references cited.

ROBERT E. BAGWILL, Primary Examiner